United States Patent
Feng et al.

(10) Patent No.: US 11,872,057 B2
(45) Date of Patent: Jan. 16, 2024

(54) ANNULAR MAPPING CATHETER

(71) Applicant: SYNAPTIC MEDICAL (BEIJING) CO. LTD., Beijing (CN)

(72) Inventors: Ji Feng, Beijing (CN); Jie Gong, Beijing (CN); Lirong Wang, Beijing (CN)

(73) Assignee: SYNAPTIC MEDICAL (BEIJING) CO. LTD., Beijing (CN)

( * ) Notice: Subject to any disclaimer, the term of this patent is extended or adjusted under 35 U.S.C. 154(b) by 779 days.

(21) Appl. No.: 16/963,804

(22) PCT Filed: Jan. 22, 2019

(86) PCT No.: PCT/CN2019/072634
§ 371 (c)(1),
(2) Date: Jul. 21, 2020

(87) PCT Pub. No.: WO2019/141284
PCT Pub. Date: Jul. 25, 2019

(65) Prior Publication Data
US 2020/0359967 A1    Nov. 19, 2020

(30) Foreign Application Priority Data
Jan. 22, 2018   (CN) .................. 201810058930.0

(51) Int. Cl.
*A61B 5/00* (2006.01)
*A61B 18/02* (2006.01)
(Continued)

(52) U.S. Cl.
CPC ............ *A61B 5/6853* (2013.01); *A61B 18/02* (2013.01); *A61B 2017/00331* (2013.01);
(Continued)

(58) Field of Classification Search
CPC ........... A61B 2018/00839; A61B 2018/00351; A61B 2018/00385; A61B 2018/00386;
(Continued)

(56) References Cited

U.S. PATENT DOCUMENTS

| | | | |
|---|---|---|---|
| 2008/0058765 A1 | 3/2008 | Jais et al. | |
| 2010/0087848 A1* | 4/2010 | Kim | A61B 18/1492 606/191 |

(Continued)

FOREIGN PATENT DOCUMENTS

| | | |
|---|---|---|
| CN | 1942145 A | 4/2007 |
| CN | 202020439 U | 11/2011 |

(Continued)

OTHER PUBLICATIONS

International Search Report issued in application No. PCT/CN2019/072634, dated Apr. 24, 2019.
(Continued)

*Primary Examiner* — Eun Hwa Kim
(74) *Attorney, Agent, or Firm* — Hamre, Schumann, Mueller & Larson, P.C.

(57) ABSTRACT

An annular mapping catheter includes a catheter body. The catheter body has a distal end and a proximal end. The distal end of the catheter body is provided with a distal end assembly, and the proximal end of the catheter body is provided with a handle. The distal end assembly is made of a head end catheter that has a shape memory function. The distal end assembly in a free state presents a predetermined bent shape including an annular part and a vertical part. The vertical part connects the annular part to the catheter body. The distal end assembly is provided with an electrode. The annular mapping catheter can detect an electrocardiogram activity near a pulmonary vein ostium and can better locate a cryoballoon in the heart.

13 Claims, 3 Drawing Sheets

(51) Int. Cl.
*A61B 17/00* (2006.01)
*A61B 18/00* (2006.01)

(52) U.S. Cl.
CPC .............. *A61B 2017/00867* (2013.01); *A61B 2018/0022* (2013.01); *A61B 2018/00375* (2013.01); *A61B 2018/00577* (2013.01); *A61B 2018/0212* (2013.01)

(58) Field of Classification Search
CPC   A61B 2018/00398; A61B 2018/00404; A61B 2018/0212
See application file for complete search history.

(56) References Cited

U.S. PATENT DOCUMENTS

| | | | | |
|---|---|---|---|---|
| 2014/0249556 | A1* | 9/2014 | Warnking | A61B 17/2202 606/169 |
| 2015/0018809 | A1* | 1/2015 | Mihalik | A61B 18/02 606/21 |
| 2016/0067528 | A1* | 3/2016 | Boegeman | A61B 5/25 606/28 |
| 2016/0302857 | A1* | 10/2016 | Rothman | A61B 18/1492 |

FOREIGN PATENT DOCUMENTS

| | | |
|---|---|---|
| CN | 105848716 A | 8/2016 |
| CN | 106413610 A | 2/2017 |
| EP | 3120792 | 1/2017 |

OTHER PUBLICATIONS

European Office Action, issued in the corresponding European patent application No. 19740717.4, dated Sep. 7, 2022, 6 pages.

Extended European Search rReport, issued in the corresponding European patent application No. 19740717.4, dated Sep. 27, 2022, 11 pages.

* cited by examiner

ANNULAR MAPPING CATHETER

TECHNICAL FIELD

The present invention relates to an annular mapping catheter for mapping a pulmonary vein ostium during ablation surgery.

BACKGROUND

Atrial fibrillation (AF) is one of the most common tachyarrhythmias in clinic. At present, for patients with paroxysmal atrial fibrillation, the ablation strategy of implementing circumferential pulmonary vein ablation and realizing electrical isolation of pulmonary veins as the final objectives has been accepted by various electro-physiological centers and has become the main and cornerstone surgery. Catheter ablation is currently the most widely used method at home and abroad. Catheter ablation is divided into two categories according to different ablation energy sources: radiofrequency ablation and cryoablation. The two categories are intended to isolate or bypass myocardial tissues that interfere with normal cardiac electrical activities, and restore normal cardiac electrical conduction. The difference is that the former leads to the degeneration and necrosis of target cells by electrocautery, and the latter is achieved by quick temperature drop in such a way that a refrigerant is evaporated to absorb a large amount of heat from the tissues.

In recent years, the cryoablation has made a great progress in the treatment of atrial fibrillation. The intracardiac annular mapping catheter used with a cryoablation catheter reaches a pulmonary vein ostium through a dedicated channel provided by the cryoablation catheter to detect the cardiac electrical activity at the pulmonary vein ostium. Due to the limitations of the head structure, the existing widely used intracardiac annular mapping catheter cannot measure the cardiac electrical activity of the ablation point at a closer distance, and the intracardiac mapping position of the catheter is also inconvenient to determine, which increase the complexity of diagnosis to a certain extent.

Therefore, a new type of annular mapping catheter is needed.

SUMMARY OF THE INVENTION

The present invention provides an annular mapping catheter, characterized in that, the annular mapping catheter comprises a catheter body, wherein the catheter body has a distal end and a proximal end, a distal assembly is disposed at the distal end of the catheter body, and a handle is disposed at the proximal end of the catheter body; the distal assembly is composed of a head tube having a shape memory function, and the distal assembly presents a predetermined bend comprising an annular portion and a vertical portion in a free state, and the vertical portion connects the annular portion to the catheter body; and the distal assembly is provided with electrodes.

Preferably, the head tube comprises a shape memory material.

Preferably, the shape memory material is a metal wire made of shape memory material.

Preferably, the metal wire extends within the predetermined bend, and a proximal end of the metal wire is fixed to the catheter body.

Preferably, the head tube comprises a flexible tube body, the shape memory material is disposed in the flexible tube body, and the electrodes are disposed outside the flexible tube body.

Preferably, the predetermined bend is formed such that, in a free state, the vertical portion extends toward the distal end at least partially beyond the annular portion.

Preferably, the annular mapping catheter is adapted to be used with a cryoballoon catheter.

Preferably, during operation, the distal assembly is pushed to extend to the distal end of a balloon through the catheter body of the cryoballoon catheter, and the annular portion extends from a hole at the distal end of the balloon.

Preferably, when the distal assembly is continuously pushed, the distal assembly extends out of the hole at the distal end of the balloon and is turned into the predetermined bend.

Preferably, after the distal assembly is turned into the predetermined bend, the annular portion abuts the positions of an effective ablation ring of the balloon.

Preferably, after the distal assembly is turned into the predetermined bend, the straight line where the vertical portion is located is perpendicular or substantially perpendicular to the plane formed by the annular portion.

Preferably, the straight line passes through the center of the annular portion.

Preferably, the cryoballoon catheter is continuously pushed, so that the annular portion is pressed against a pulmonary vein ostium for mapping.

Preferably, two groups of electrodes are distributed on the distal assembly.

Preferably, the annular portion of the distal assembly is provided with one group of electrodes, and the vertical portion of the distal assembly is provided with the other group of electrodes.

Preferably, the electrodes on the vertical portion cooperate with the electrodes on the annular portion to position the balloon.

Preferably, the electrodes on the annular portion are used to map the pulmonary vein ostium.

Preferably, the vertical portion is provided with at least two electrodes.

Preferably, the annular portion is provided with a plurality of electrodes distributed uniformly.

Preferably, after the distal assembly is turned from the annular structure into the predetermined bend, the at least two electrodes on the vertical portion form a straight line, and the electrodes on the annular portion form a plane; and the straight line formed by the at least two electrodes on the vertical portion is perpendicular or substantially perpendicular to the plane formed by the electrodes on the annular portion.

Preferably, the straight line formed by the at least two electrodes on the vertical portion passes through the circle center of the annular portion.

Preferably, the distances between the at least two electrodes on the vertical portion and the electrodes on the annular portion are constant.

Preferably, after the distal assembly is turned into the predetermined bend, a development marker is disposed at the most distal end of the predetermined bend.

According to the present invention, it is provide a cryoablation device, comprising: an annular mapping catheter, comprising a catheter body, wherein the catheter body has a distal end and a proximal end, a distal assembly is disposed at the distal end of the catheter body, and a handle is disposed at the proximal end of the catheter body; the distal assembly is composed of a head tube having a shape memory function, and the distal assembly presents a predetermined bend comprising an annular portion and a vertical portion in a free state, and the vertical portion connects the annular portion to the catheter body; and the distal assembly is provided with electrodes; and a cryoballoon catheter, wherein the annular mapping catheter is adapted to be used with the cryoballoon catheter.

Preferably, the predetermined bend is formed such that, in a free state, the vertical portion extends toward the distal end at least partially beyond the annular portion; the distal assembly is pushed to extend to the distal end of a balloon through the catheter body of the cryoballoon catheter, and the annular portion extends from a hole at the distal end of the balloon.

Preferably, when the distal assembly is continuously pushed, the distal assembly extends out of the hole at the distal end of the balloon and is turned into the predetermined bend, and the annular portion abuts the positions of an effective ablation ring of the balloon.

Preferably, after the distal assembly is turned into the predetermined bend, the straight line where the vertical portion is located is perpendicular or substantially perpendicular to the plane formed by the annular portion.

Preferably, the straight line passes through the circle center of the annular portion.

Preferably, the annular portion of the distal assembly is provided with one group of electrodes, and the vertical portion of the distal assembly is provided with another group of electrodes; and the electrodes on the vertical portion cooperate with the electrodes on the annular portion to position the balloon.

Preferably, the vertical portion is provided with at least two electrodes, and the annular portion is provided with a plurality of electrodes distributed uniformly.

Preferably, after the distal assembly is turned from the annular structure into the predetermined bend, the at least two electrodes on the vertical portion form a straight line, and the electrodes on the annular portion form a plane; and the straight line formed by the at least two electrodes on the vertical portion is perpendicular or substantially perpendicular to the plane formed by the electrodes on the annular portion.

Preferably, the straight line formed by the at least two electrodes on the vertical portion passes through the circle center of the annular portion.

Preferably, the distances between the at least two electrodes on the vertical portion and the electrodes on the annular portion are constant.

Preferably, after the distal assembly is turned into the predetermined bend, a development marker is disposed at the most distal end of the predetermined bend.

In a preferred embodiment of the present invention, the annular mapping catheter can detect the cardiac electrical activity near the pulmonary vein ostium, and can also better locate the position of a cryoballoon in the heart.

BRIEF DESCRIPTION OF THE DRAWINGS

The present invention will be more fully understood through the following detailed descriptions and the accompanying drawings, in which similar elements are numbered in a similar manner, wherein.

DETAILED DESCRIPTION OF EMBODIMENTS

The technical solution of the present invention will be further described in detail below through embodiments and in combination with the accompanying drawings, but the present invention is not limited to the embodiments below.

Figure 1:
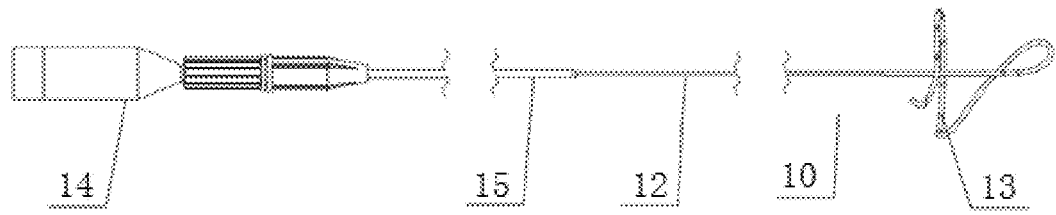
FIG. 1 is a schematic structural diagram of an annular mapping catheter according to an embodiment of the present invention.

FIG. 1 is a schematic structural diagram of an annular mapping catheter 10 according to an embodiment of the present invention, including a catheter body 12 having a distal end and a proximal end, with a distal assembly 13 being disposed at the distal end of the catheter body 12. In some embodiments, the catheter body 12 may be made of a metal material, such as stainless steel, which can enhance the support force of the tube body. Other suitable materials are also feasible. A handle 14 is disposed at the proximal end of the catheter body 12, and the handle 14 facilitates the operation on the annular mapping catheter 10 and can be used as a catheter connecting seat of the catheter body 12. A guide tube 15 may be sleeved on the proximal end of the catheter body 12. The guide tube 15 is adapted to guide the annular mapping catheter 10 into a cryoballoon catheter 20.

Figure 2:
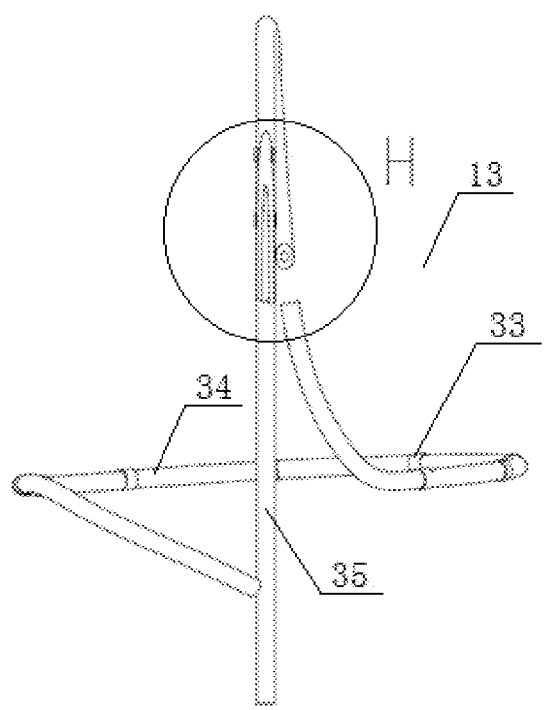
FIG. 2 is a schematic diagram of a distal structure of the annular mapping catheter.
Figure 3:
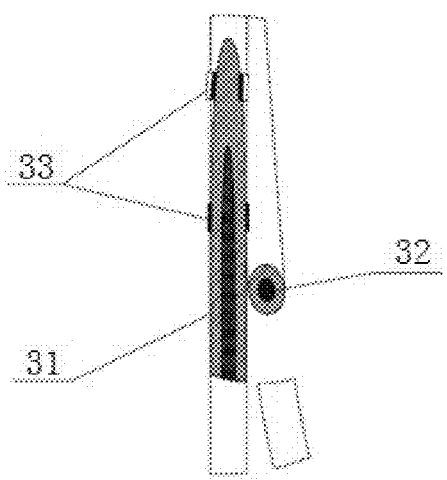
FIG. 3 is an enlarged view of part H in FIG. 2.
Figure 4:
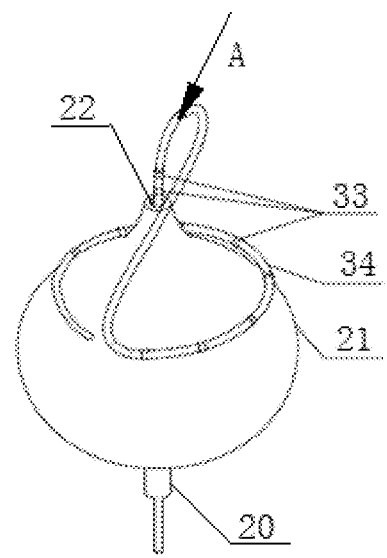
FIG. 4 is a schematic diagram showing that the annular mapping catheter is used with a cryoballoon catheter according to an embodiment of the present invention.

FIG. 2 is a schematic structural diagram of the distal assembly 13 of the annular mapping catheter 10, and FIG. 3 is an enlarged view of part H in FIG. 2. As shown in FIG. 2 and FIG. 3, the distal assembly 13 may be composed of a head tube (tube at the head end) 31. For example, the distal assembly 13 is constructed by rotating the head tube 31 and has a predetermined bend, wherein the predetermined bend may include an annular portion 34 and a vertical portion 35. The proximal end of the head tube 31 may be fixed to the catheter body 12 in any suitable manner, for example, by bonding. According to a preferred embodiment of the present invention, as shown in FIG. 2 or FIG. 4, the predetermined bend is formed such that, in a free state, the vertical portion extends toward the distal end at least partially beyond the annular portion. That is, as described below, when the predetermined bend of the distal assembly 13 extends and passes through the catheter body of the cryoballoon catheter cooperating therewith, the annular portion 34 can be turned backward from the vertical portion 35 and then abut on the positions corresponding to an effective ablation ring on a balloon of the cryoballoon catheter. The effective ablation ring may refer to a circle B with a low cryogenic temperature on the surface of the balloon, or a circle C where the distal end of the balloon contacts myocardial tissues when the balloon abuts pulmonary veins, or a circle D where the annular portion 34 contacts the balloon after the distal assembly 13 is turned into the predetermined bend. The circle B, the circle C, and the circle D may be coincident or substantially coincident.

The vertical portion 35 is a portion that connects the annular portion 34 to the catheter body 12. As can be seen from the figures, the vertical portion 35 may include a substantially linear portion connected to the catheter body 12 and a bent portion connected to the annular portion, and is generally vertical in a free state relative to the annular portion 34.

The annular portion 34 is of an annular shape, and can also be set by those skilled in the art to be substantially annular as needed, which can also achieve the same technical effect without departing from the spirit of the present invention. The annular portion 34 may also be of a polygonal structure. The central axis of the annular portion 34 may be in line with the axis of the proximal portion of the head tube 31, or offset from the axis of the proximal portion of the head tube 31.

The head tube 31 may include a tube body and the shape memory material inside the tube body, and thus has a shape memory function. The tube body can be made of a biocompatible material, and includes a distal end, a proximal end, and a central chamber. The tube body is usually flexible, and the shape memory material extends in the central chamber of the tube body, so that the head tube 31 also has a shape memory function. According to an embodiment of the present invention, a metal wire 32 extends inside the central chamber of the tube body of the head tube 31. The wire 32 may be made of a shape memory material, such as nickel-titanium alloy. The distal end of the wire 32 extends to the distal end of the head tube 31 and is fixed, for example, by bonding. The proximal end of the wire 32 is fixed to the catheter body 12, for example, by bonding or welding. Since the wire 32 is fixedly connected to the tube body of the head tube 31, the head tube 31 has the same memory function as the wire 32. When the shape of the tube body of the head tube 31 is changed, the original shape can be restored in a short time, and the wire 32 can also provide good support performance to the tube body of the head tube 31.

In some embodiments, the wire 32 is fixed to the tube body of the head tube 31 over the entire length, so that the head tube 31 has a better shape memory function. In some other embodiments, due to the tight fit between the wire and the flexible tube body, no additional fixing means is required, and the head tube 31 may also have a good shape memory function.

Preferably, the wire 32 extends along the entire predetermined bend. The shape of the wire 32 is not limited, as long as it can cooperate with the tube body of the head tube 31 so that the head tube 31 has a shape memory function.

As described above, the distal assembly 13 presents a predetermined bend including the annular portion 34 and the vertical portion 35 in a free state. The vertical portion 35 connects the annular portion to the catheter body 12.

The distal assembly 13 is also provided with electrodes 33, and the number of the electrodes 33 may be determined according to actual needs. The electrodes 33 can either transmit signals or be used for positioning. According to an embodiment of the present invention, two groups of electrodes are distributed on the distal assembly 13, which are disposed on the annular portion 34 and the vertical portion 35 respectively. The number of electrodes on the annular portion 34 may be determined according to actual needs. The electrodes 33 may be distributed uniformly, or the spacing between the electrodes may be determined as required. Preferably, a plurality of electrodes distributed uniformly are disposed on the annular portion 34. At least two electrodes are disposed on the vertical portion 35, and the at least two electrodes can be used for positioning the balloon or for mapping, as described in detail below. When a related surgical operation is performed, the positions and shapes of the annular portion 34 and the vertical portion 35 can be determined through these electrodes on a three-dimensional detector.

According to an embodiment of the present invention, the distal end of a conductor wire (not shown in the figures) extends into the chamber of the head tube 31 through the central chamber of the catheter body 12, and is electrically connected to the electrodes 33. The proximal end of the conductor wire is fixed to the handle 14 by any suitable method known to those skilled in the art, for example, by welding to a corresponding plug. Signals measured by the electrodes 33 can be obtained through the plug for corresponding analysis.

FIG. 4 is a schematic diagram showing that the annular mapping catheter 10 is used with a cryoballoon catheter 20 according to an embodiment of the present invention. The catheter body of the cryoballoon catheter 20 is used to guide the annular mapping catheter 10. As shown in FIG. 4, when the annular mapping catheter 10 is used, the distal assembly 13 extends to a balloon 21 through the catheter body of the cryoballoon catheter 20, and contracts within the balloon 21. After the distal assembly 13 extends out of a hole 22, the annular portion 34 is restored to an annular structure due to the shape memory function. At this time, a pulmonary vein ostium can be initially mapped to diagnose whether the tissue here is a focal point, and part A in FIG. 4 is still within the balloon at this time. Next, the cryoballoon catheter 20 performs cryoablation on the tissue. When the ablation is completed, the cryoballoon catheter 20 can be withdrawn into the left atrium, the distal assembly 13 can be continuously pushed from the hole 22 at the distal end of the balloon 21, and part A in FIG. 4 extends out of the balloon. At this time, the bend of the distal assembly 13 is turned from the initial annular structure into the predetermined bend, that is, the predetermined bend including the annular portion 34 and the vertical portion 35. Then, the distal assembly 13 is withdrawn, so that the annular portion 34 abuts the position of the effective ablation ring of the balloon 21, that is, the position with the lowest temperature on the cryoballoon. The cryoballoon catheter 20 is pushed forward so that the annular portion 34 is pressed against the pulmonary vein ostium, and the tissue here can be mapped by the electrodes on the annular portion 34 to judge whether the ablation is successful.

The electrodes 33 on the vertical portion 35 may cooperate with the electrodes on the annular portion 34 to locate the positions of the balloon 21. Specifically, after the bend of the distal assembly 13 is turned from the initial annular structure to the predetermined bend, the at least two electrodes on the vertical portion 35 form a straight line, and the straight line may be in line with or substantially in line with the axis of the catheter 10. The electrodes on the annular portion 34 form a plane. The straight line formed by the at least two electrodes on the vertical portion 35 is perpendicular or substantially perpendicular to the plane formed by the electrodes on the annular portion 34, and the straight line passes through the circle center of the annular portion 34 or substantially passes through the circle center of the annular portion 34. The distances between the two electrodes on the vertical portion 35 and the electrodes on the annular portion 34 are constant. Therefore, the height, length, angle and the like of the geometry formed by the connecting lines between the two electrodes on the vertical portion 35 and the electrodes on the annular portion 34 are constant, and the shape and position of the geometry can be determined in a three-dimensional system during operation. Since the annular portion 34 is at the position of the effective ablation ring of the balloon 21, the balloon can be positioned in the three-dimensional system. That is to say, after the bend of the distal assembly 13 is turned from the initial annular structure into the predetermined bend, the straight line where the vertical portion 35 is located is perpendicular or substantially perpendicular to the plane formed by the annular portion 34, and the straight line passes through the circle center of the annular portion 34 or substantially passes through the circle center of the annular portion 34.

That is, according to the embodiment of the present invention, during operation, the distal assembly 13 can be pushed to extend to the distal end of the balloon through the body of the cryoballoon catheter 20, and the annular portion 34 extends from the hole at the distal end of the balloon. When the distal assembly is continuously pushed, the distal assembly 13 extends out of the hole at the distal end of the balloon and is turned into the predetermined bend. After the distal assembly 13 is turned into the predetermined bend, the annular portion 34 abuts the position of the effective ablation ring of the balloon. Thereafter, the cryoballoon catheter can be pushed forward so that the annular portion 34 is pressed against the pulmonary vein ostium, and the tissue here can be mapped by the electrodes on the annular portion 34 to judge whether the ablation is successful.

Figure 5:
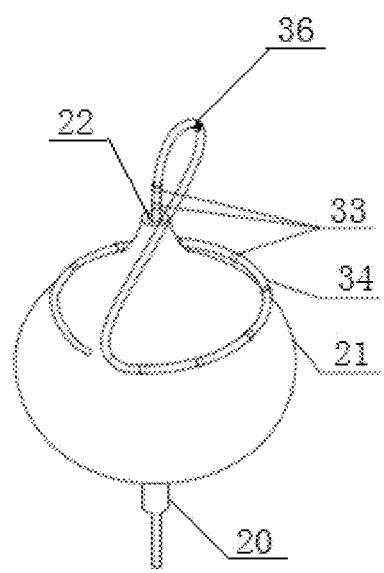
FIG. 5 is a schematic diagram of a modified embodiment of the embodiment shown in FIG. 4.

FIG. 5 is a modified embodiment of the embodiment shown in FIG. 4. Except that a development marker 36 is added, other aspects are basically the same as those in FIG. 4. As shown in the figure, after the distal assembly 13 is turned into the predetermined bend, a development marker 36 is disposed at the farthest or substantially farthest position of the predetermined bend, and the development marker 36 may be a development ring or other suitable structure. The set of the development marker 36 causes that, during the distal end of the annular mapping catheter 10 is fed into the pulmonary vein ostium, to the development marker 36 may display the position of the distal end of the catheter in real time and display whether the distal end of the catheter reaches the pulmonary vein ostium. According to the position of the development marker 36, it can also be judged whether the bend of the distal assembly 13 is turned from the initial annular structure into the predetermined bend.

The embodiments of the present invention are not limited to the above embodiments. Persons of ordinary skill in the art may make various changes and improvements to the present invention in form and details without departing from the spirit and scope of the present invention, and these changes and improvements are considered to fall within the protection scope of the present invention.

What is claimed is:

1. An annular mapping catheter, wherein the annular mapping catheter is adapted to be used with a cryoballoon catheter, the annular mapping catheter comprising:
    a catheter body, wherein the catheter body has a distal end and a proximal end;
    a handle disposed at the proximal end of the catheter body;
    a distal assembly disposed at the distal end of the catheter body, the distal assembly including a head tube having a flexible tube body and a shape memory material, and the distal assembly presents a predetermined bend comprising an annular portion and a vertical portion in a free state, and the vertical portion connects the annular portion to the catheter body, and the distal assembly is provided with electrodes,
    wherein the predetermined bend is formed such that, in a free state, the vertical portion extends toward the distal end at least partially beyond the annular portion and the end of the annular portion slants toward the proximal end,
    wherein after the distal assembly is turned into the predetermined bend, a development marker is disposed at the most distal end of the predetermined bend, and
    wherein during operation, the distal assembly is configured to extend from a hole at a distal end of a balloon of the cryoballoon catheter, and transitions into the predetermined bend, the cryoballoon catheter is configured to move distally towards the annular portion of the distal assembly such that the annular portion is in contact with a distal portion of the balloon for pulmonary vein ostium mapping and cryoablation.

2. The annular mapping catheter according to claim 1, wherein after the distal assembly is turned into the predetermined bend, a straight line where the vertical portion is located is perpendicular or substantially perpendicular to a plane formed by the annular portion.

3. The annular mapping catheter according to claim 2, wherein the straight line passes through the center of the annular portion.

4. The annular mapping catheter according to claim 1, wherein two groups of the electrodes are distributed on the distal assembly, wherein the annular portion of the distal assembly is provided with a first group of the electrodes, and the vertical portion of the distal assembly is provided with a second group of the electrodes.

5. The annular mapping catheter according to claim 4, wherein the second group of the electrodes on the vertical portion cooperate with the first group of the electrodes on the annular portion to position the balloon.

6. The annular mapping catheter according to claim 5, wherein the first group of the electrodes on the annular portion are used to map the pulmonary vein ostium.

7. The annular mapping catheter according to claim 6, wherein the first group of the electrodes on the annular portion are distributed uniformly.

8. The annular mapping catheter according to claim 7, wherein
    the second group of the electrodes on the vertical portion forms a straight line and the first group of the electrodes on the annular portion form a plane, and the straight line formed by the second group of the electrodes is perpendicular or substantially perpendicular to the plane formed by the first group of the electrodes.

9. The annular mapping catheter according to claim 8, wherein the straight line formed by the second group of the electrodes passes through a circle center of the annular portion, wherein distances between the first group of the electrodes and the second group of the electrodes are constant.

10. A cryoablation device, comprising:
    an annular mapping catheter comprising:
        a catheter body, wherein the catheter body has a distal end and a proximal end,
        a handle is disposed at the proximal end of the catheter body,
        a distal assembly disposed at the distal end of the catheter body, the distal assembly including a head tube having a flexible tube body and a shape memory material, and the distal assembly presents a predetermined bend comprising an annular portion and a vertical portion in a free state, and the vertical portion connects the annular portion to the catheter body, and the distal assembly is provided with electrodes; and
    a cryoballoon catheter, wherein the annular mapping catheter is adapted to be used with the cryoballoon catheter,
    wherein the predetermined bend is formed such that, in a free state, the vertical portion extends toward the distal end at least partially beyond the annular portion and the end of the annular portion slants toward the proximal end;

wherein after the distal assembly is turned into the predetermined bend, a development marker is disposed at the most distal end of the predetermined bend; and wherein during operation, the distal assembly is configured to extend from a hole at a distal end of a balloon of the cryoballoon catheter, and transitions into the predetermined bend, the cryoballoon catheter is configured to move distally towards the annular portion of the distal assembly such that the annular portion is in contact with a distal portion of the balloon for pulmonary vein ostium mapping and cryoablation.

11. The cryoablation device according to claim 10, wherein after the distal assembly is turned into the predetermined bend, a straight line where the vertical portion is located is perpendicular or substantially perpendicular to a plane formed by the annular portion.

12. The cryoablation device according to claim 10,
wherein the annular portion of the distal assembly is provided with a first group of the electrodes, and the vertical portion of the distal assembly is provided with a second group of the electrodes; and wherein the second group of the electrodes on the vertical portion cooperate with the first group of the electrodes on the annular portion to position the balloon and the first group of electrodes on the annular portion are distributed uniformly.

13. The cryoablation device according to claim 12, wherein the second group of the electrodes on the vertical portion form a straight line and the first group of the electrodes on the annular portion form a plane, and the straight line formed by the second group of the electrodes is perpendicular or substantially perpendicular to the plane formed by the first group of the electrodes on the annular portion.

\* \* \* \* \*